United States Patent
Steude et al.

(10) Patent No.: US 9,945,823 B2
(45) Date of Patent: Apr. 17, 2018

(54) DEVICE AND METHOD FOR COMBUSTION ANALYSIS BY MEANS OF INDUCTION FURNACES AND PROTECTIVE ELEMENT FOR INDUCTION FURNACES FOR THE COMBUSTION ANALYSIS

(75) Inventors: Martin Steude, Kamp-Lintfort (DE); Christian Camps, Grefrath (DE)

(73) Assignee: BRUKER AXS GMBH, Karlsruhe (DE)

( * ) Notice: Subject to any disclaimer, the term of this patent is extended or adjusted under 35 U.S.C. 154(b) by 802 days.

(21) Appl. No.: 13/989,368

(22) PCT Filed: Nov. 23, 2011

(86) PCT No.: PCT/DE2011/075286
§ 371 (c)(1),
(2), (4) Date: Aug. 12, 2013

(87) PCT Pub. No.: WO2012/097784
PCT Pub. Date: Jul. 26, 2012

(65) Prior Publication Data
US 2013/0316465 A1    Nov. 28, 2013

(30) Foreign Application Priority Data

Nov. 23, 2010   (DE) .................. 10 2010 060 723
Jan. 26, 2011    (DE) .................. 10 2011 000 329

(51) Int. Cl.
*G01N 31/12*    (2006.01)

(52) U.S. Cl.
CPC .................. *G01N 31/12* (2013.01)

(58) Field of Classification Search
CPC .................................................. G01N 31/12
See application file for complete search history.

(56) References Cited

U.S. PATENT DOCUMENTS

| | | | |
|---|---|---|---|
| 2,332,943 A | 10/1943 | Sobers | |
| 2,932,558 A * | 4/1960 | Bennet | G01N 31/12 422/78 |

(Continued)

FOREIGN PATENT DOCUMENTS

| | | | |
|---|---|---|---|
| GB | 1307941 | * | 2/1973 |
| WO | 83/04310 A1 | | 12/1983 |

OTHER PUBLICATIONS

International Search Report, dated May 8, 2012, for PCT/DE2011/075286, 3 pages.

*Primary Examiner* — Krishnan S Menon
*Assistant Examiner* — Dwan A Gerido
(74) *Attorney, Agent, or Firm* — Seed IP Law Group LLP

(57) ABSTRACT

With a device for combustion analysis, comprising an induction furnace with a furnace chamber, in which carrier gas can flow during operation via at least one gas inlet to a gas outlet, and in which a sample to be analyzed can be arranged and burned in a sample container, a hollow protective element is provided and, with normal operation of the device, is arranged in the furnace chamber directly above the sample in such a way that the end of the protective element facing towards the sample, together with the sample container, forms a constriction for the carrier gas flow, wherein the protective element is desgned to convey gases produced during the combustion of the sample through the protective element and to the gas outlet.

7 Claims, 5 Drawing Sheets

(56) References Cited

U.S. PATENT DOCUMENTS

| | | | |
|---|---|---|---|
| 3,148,032 A | | 9/1964 | Bennet et al. |
| 3,172,647 A | * | 3/1965 | Remmey ............... F27B 9/3011 |
| | | | 432/133 |
| 4,116,632 A | * | 9/1978 | Kaartinen ............... G21F 9/007 |
| | | | 422/78 |
| 4,213,763 A | | 7/1980 | Madec et al. |
| 4,668,479 A | * | 5/1987 | Manabe .................. B05B 7/222 |
| | | | 118/715 |
| 4,784,833 A | | 11/1988 | Martin |
| 6,309,446 B1 | * | 10/2001 | Nakanoya ................ B01J 20/20 |
| | | | 502/418 |
| 2008/0026471 A1 | | 1/2008 | Lorant |

* cited by examiner

DEVICE AND METHOD FOR COMBUSTION ANALYSIS BY MEANS OF INDUCTION FURNACES AND PROTECTIVE ELEMENT FOR INDUCTION FURNACES FOR THE COMBUSTION ANALYSIS

TECHNICAL FIELD OF THE INVENTION

The invention relates to a device and to a method for combustion analysis by means of induction furnaces, wherein a sample, in particular an inorganic sample, is burned in an induction furnace and the gases produced during the combustion process are analyzed. The invention also relates to a protective element for retrofitting or refitting induction furnaces for the combustion analysis.

BACKGROUND OF THE INVENTION

In order to establish the composition of inorganic samples by means of combustion, in particular the composition of materials such as steel, iron, nonferrous metals, aluminum, titanium, zirconium, ores and alloys of the aforementioned substances, ceramic materials, cement, lime and the like, various methods and devices are known, with which a sample is in each case burned in an induction furnace and the combustion gases are analyzed automatically by means of corresponding detectors.

Besides the rapid (lasting less than approximately 1 to 2 minutes) combustion of samples by inductive heating of the sample, devices and methods are also known, for example from documents US 2008/0026471 A1 and U.S. Pat. No. 4,213,763, with which the samples to be analyzed are heated relatively slowly, specifically with heating rates of approximately 25-50° C. per minute, to temperatures in the range of approximately 600-850° C. in heated furnaces in which the furnace chamber itself is heated for example by resistance heating wires, wherein gases then have to be collected and analyzed over an accordingly long period of time. This slow heating process is indeed free from or only insignificantly tainted by specific problems, in particular such as the soiling of the furnace chamber described hereinafter by sample material and a conventional reaction accelerator to be added to the sample material, said accelerator boiling up upon sudden heating and spattering out from a sample crucible, however these devices and methods are not suitable for rapid sample analysis.

With devices and methods of the type concerned here, the heat required for combustion of the sample is generated by electromagnetic induction. The sample is arranged for this purpose in a sealable inner chamber of an induction furnace, said chamber being referred to hereinafter as a furnace chamber and being provided with gas inlets and gas outlets, wherein an electromagnetic high-frequency field for induction of eddy currents is then generated in the furnace chamber, generally by means provided outside the furnace chamber.

In order to obtain combustion gases that are concentrated to the highest possible extent over a short period of time and that can be utilized better by corresponding detectors compared to gases of lower concentration, and for economical reasons, the samples are to burn as quickly as possible. Hence, so called reaction accelerators are generally added to the samples, said accelerators having good coupling to the high-frequency field and therefore ensuring rapid heating of the sample.

In order to further promote the combustion process, the samples are blasted in the known devices with oxygen via a lance arranged above the sample to be burned. The oxygen blasted at a certain overpressure into the sealed furnace chamber is then advantageously used simultaneously as a carrier gas in order to transport the combustion gases from the furnace via a gas outlet and to the respective detectors. Here, the oxygen is normally to be fed not only via the lance, but also via further gas inlets provided in the upper and in the lower region of the furnace chamber, more specifically in such a way that a net gas flow is produced upwardly, where a gas outlet is arranged, which is connected to a sample line to transport the gases from the furnace chamber to corresponding detectors.

A big problem with the known devices is posed by the material spatters produced during the combustion process. The samples are generally placed into the furnace chamber in an open ceramic crucible and boil during the analysis process, wherein sample material and reaction accelerators spatter from the crucible and soil the furnace chamber, which is generally formed by a quartz glass pipe. The direct flow of oxygen onto the sample via a lance provided in the known devices increases the problem further. During subsequent combustion analyses, the spattered material is melted again, can become baked into the walls of the furnace chamber and in particular of a quartz glass pipe forming the furnace chamber and/or can falsify the measurement results. Baked spattered material results after a short time in destruction of the quartz glass pipe.

In order to prevent the spattered material from clogging the gas inlets and gas outlets provided in the respective furnace chamber, the gas inlets and gas outlets in the known combustion furnaces, with the exception of the lance arranged directly above the sample, are arranged as far as possible from the sample itself in the respective furnace chamber: This means however that the furnace chambers in the known combustion furnaces are relatively large, which entails a whole series of disadvantages. In the known devices, the combustion gases therefore diffuse initially in the entire furnace chamber and mix with the oxygen fed as carrier gas before they reach the gas outlet, and therefore the concentration of the combustion gases is low and only some of the available oxygen comes into contact with the sample.

The volume of the furnace chamber also influences the duration of a measurement cycle, since on the one hand it is to be ensured that the total amount of combustion gases is conveyed to the detectors where possible, and on the other hand the device has to be flushed with a gas, generally oxygen, between two successive measurements. The downtimes between two successive measurements in the known devices are typically between approximately 100 and 180 seconds, and the analysis times are typically between 120 and 140 seconds.

If the flow rate is increased, the analysis times are radically reduced (if the flow rate is doubled, the analysis time is approximately halved). However, an increase in the flow rate leads to a significant distortion of the measurement signal, whereby the measurement accuracy of the device is considerably lowered. For this reason, the flow rate is not increased in conventional devices.

In order to minimize the spatter formation, tungsten is generally used as a reaction accelerator. The tungsten couples well to the high-frequency field, melts quickly, and thus binds the sample material, which is generally in chip or powder form.

Approximately 1 g of tungsten is typically added to a sample quantity of approximately 0.5 to 1 g.

The use of tungsten entails a whole series of disadvantages however. During the combustion process, a fine tungsten oxide powder is produced, which soils the combustion furnace and the sample line. In the known devices, at least one filter for coarse particles and a filter for fine particles are therefore generally arranged in the sample line. Since tungsten oxide is harmful to health, specific precautionary measures must be taken when cleaning the combustion furnace and in particular the combustion chamber and the filter arrangement, and also when loading and unloading the furnace chamber. The tungsten oxide has to be disposed of separately. In addition, tungsten is expensive to purchase.

Theoretically, substances that can be handled more easily, such as pure iron in particular, could also be used as reaction accelerators. Pure iron couples very effectively to a high-frequency field in the furnace, is not harmful to health, and is additionally more cost effective compared to tungsten. However, substances such as pure iron spatter much more severely during heating compared to tungsten, and therefore considerably more and hotter particle spatters are produced, which bake more quickly into the furnace wall, clog gas inlets and gas outlets, and are difficult to remove. If the furnace chamber is formed by a quartz glass pipe, as is conventional, the service life of the quartz glass pipe is reduced so severely by the use of pure iron that the use of pure iron is not sensible from an economical point of view.

DISCLOSURE OF THE INVENTION

The object of the invention is to specify a device and a method for combustion analysis by means of induction furnaces, which make it possible to considerably lengthen the service lives of the furnace chambers, to carry out the combustion process at higher temperatures, and at the same time to drastically reduce the analysis times, the cleaning effort, the carrier gas consumption and also the downtimes between two successive measurements.

The object is achieved by a device comprising an induction furnace with a furnace chamber, in which carrier gas can flow during operation via at least one gas inlet to a gas outlet, and in which a sample to be analyzed can be arranged and burned in a sample container, wherein a hollow protective element is provided and, with normal operation of the device, is arranged in the furnace chamber directly above the sample in such a way that the end of the protective element facing towards the sample, together with the sample container, forms a constriction for the carrier gas flow, wherein the protective element is designed to convey gases produced during the combustion of the sample through the protective element and to the gas outlet.

The protective element advantageously performs a number of functions: It intercepts any material spatters produced during the combustion process and thus protects the furnace chamber, it collects the gases produced during the combustion of a sample directly above the point of combustion and forwards them on, such that said gases reach a gas outlet in highly concentrated form, and, together with a sample container, it forms a constriction for a carrier gas flow, such that the sample can be blasted selectively and it is possible to dispense with the previously conventional lance for blasting the sample. Since hot material spatters are then no longer problematic, the protective element allows higher combustion temperatures, typically in the region of 1,500° C., and therefore makes it possible to use pure iron for example as a reaction accelerator, pure iron being much more easily handled, in particular from health aspects, and additionally being more cost effective than tungsten.

It has surprisingly been found that satisfactory combustion results can then also be achieved when the sample is not blasted directly with carrier gas, generally oxygen, using a lance. If the lance is omitted, the combustion gases can be collected directly above the point of combustion, such that the gases are not first mixed with oxygen present in the furnace chamber and advantageously reach the downstream detectors in a more highly concentrated form, which enables a more accurate analysis. It has been found that the detectors then deliver signals that are 100 to 150% stronger than in known devices. In addition, the flow rate times reduce drastically.

Since the gas inlets are now protected against spatters, the volume of the furnace chambers can be reduced, which, inter alia, causes a lower gas consumption during the measurement process and when flushing the chambers, but in particular also reduces the downtimes between two measurements and therefore further increases the economic viability of the device. First tests show that, with a device according to the invention, the measurement times and downtimes can be reduced by 30 to 60% compared to those of conventional devices.

The protective element may advantageously consist of a suitable ceramic, in particular of a ceramic containing silicon nitride. A protective element that consists substantially of silicon nitride can be easily cleaned as required since spatters are virtually not baked in.

The spacing of the sample container from the protective element can be adjusted. Since the sample container is normally a crucible, which is positioned on a sample carrier, the gap between the upper crucible edge and the diffusor can be selected such that on the one hand any material spattering out from the crucible during combustion of the sample is collected as far as possible by the protective element and the furnace chambers are not soiled, and on the other hand it is ensured that sufficient oxygen reaches the sample in the crucible.

The gap and the protective element together cause a jet or flue effect, such that oxygen from the furnace chamber flows selectively over the sample to be burned and the combustion gases produced are then removed above the sample. Here, it should be noted at this juncture that the combustion gases typically are not actively aspirated via the protective element, that is to say there is no suction pump downstream of the gas outlet, but rather the gases are pushed out from the furnace chamber by an overpressure via the protective element.

In terms of a method, the object is achieved by a method for combustion analysis, in which a sample to be analyzed is arranged and burned in a sample container in the furnace chamber of an induction furnace, through which a carrier gas is conveyed, wherein a hollow protective element is arranged above the sample container before combustion of the sample, in such a way that the protective element, together with the sample container, forms a constriction for the carrier gas flow, wherein the gases produced during the combustion of the sample are conveyed from the furnace chamber through the protective element.

Advantageous embodiments of the device according to the invention and implementations of the method according to the invention are disclosed in the respective dependent claims. The further independent claim, claim 15, concerns a protective element for retrofitting or refitting existing induction furnaces for combustion analyses.

Further details and advantages of the invention will emerge from the following non-limiting description of exemplary embodiments, which is provided purely by way of example and in conjunction with the drawings.

DESCRIPTION OF PREFERRED EMBODIMENTS

Figure 1:
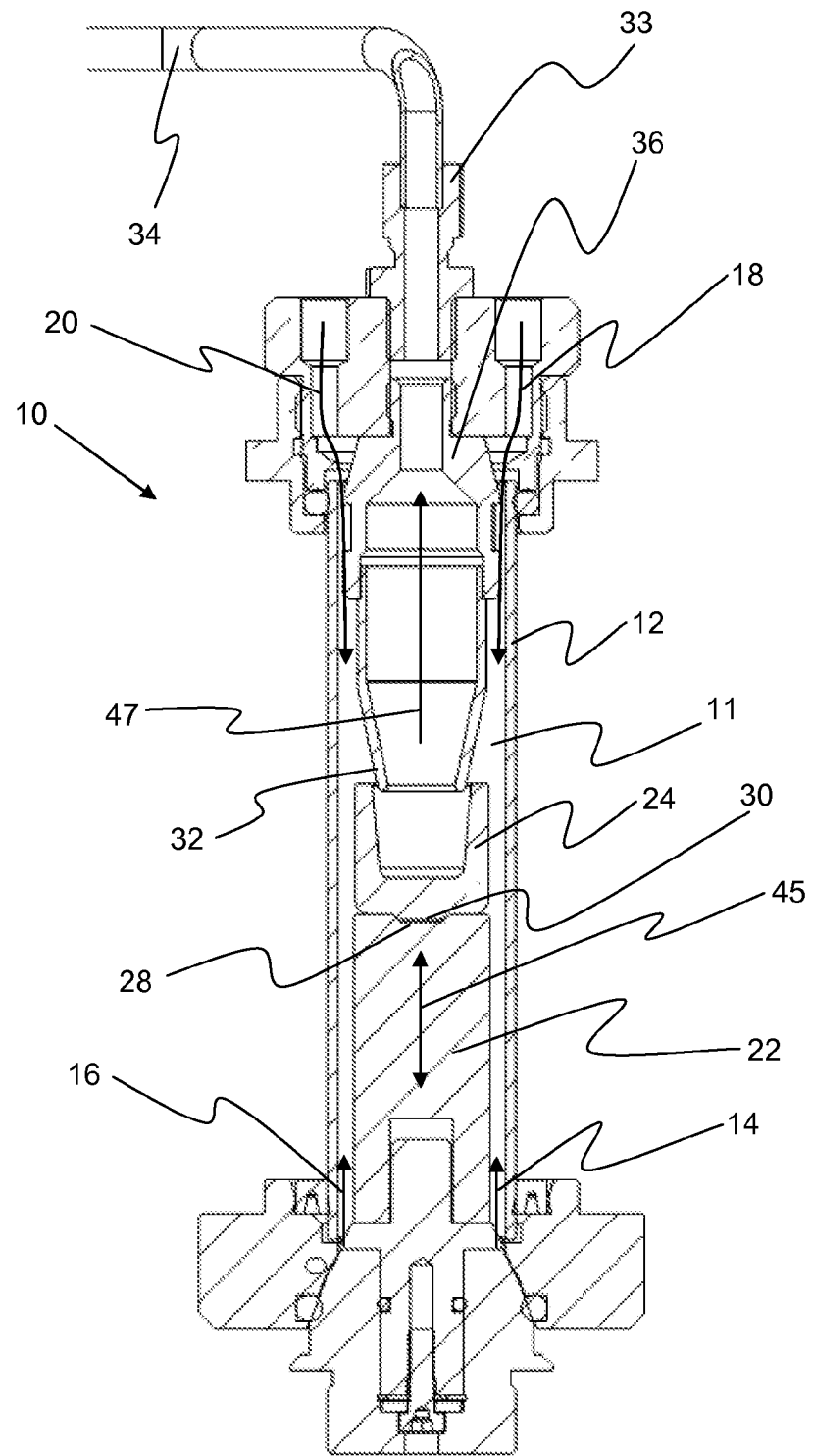
FIG. 1 shows a longitudinal section through key parts of a device formed in accordance with the invention in a first embodiment.

FIG. 1 shows a longitudinal section of a device denoted on the whole by 10, comprising an induction furnace with a furnace chamber 11 for combustion analysis, with the parts that are necessary for understanding the invention. In particular, means known per se for generating a high-frequency field in the furnace chamber 11, for example for generating a field with an excitation frequency in the range from typically approximately 10 MHz to 30 MHz, are not shown.

The furnace chamber 11 is formed in the shown exemplary embodiment in a quartz glass pipe 12, into which gas can be conveyed, as indicated by the arrows 14, 16, 18 and 20. Quartz glass has proven to be particularly effective for the induction furnaces concerned here since it is transparent for the high-frequency field and can be fabricated with very precise edges, and therefore the chamber can be easily sealed. Typical dimensions for the pipe are, for example, diameters in the range from approximately 40 to 60 mm, lengths between approximately 100 and 200 nm, and wall thicknesses in the range of 1-2 mm.

The gas conveyed through the furnace chamber is typically oxygen, which can be used both as a combustion partner during the combustion of a sample and as a carrier gas for transport of the combustion gas. For specific analysis methods, for example a slowed combustion of the sample, other gases or mixtures of gases can also be used.

In the furnace chamber 11, a movable sample carrier 22 is provided, on which the sample to be burned is arranged in a sample container that is exchangeable in this embodiment, specifically a crucible 24, which is then placed onto the sample carrier. The sample is then burned in the crucible, of which the position in the furnace chamber is determined by the sample carrier. To this end, in this exemplary embodiment, the sample carrier 22 has an indentation 28 on its side facing towards the crucible 24, and the crucible has a convexity 30, at least partially complementary to the indentation 28, on its side facing towards the sample carrier 22, and therefore the crucible 24 can be positioned easily on the sample carrier.

In the induction furnace, a protective element 32, here in the form of a diffusor, is also provided directly above the point of combustion formed here in the crucible 24 and is used to collect and forward the gases produced during the combustion of a sample, said protective element opening out into a gas outlet 33, to which a sample line 34 is connected, via which the combustion gases to be analyzed are then conveyed to detectors known per se (not illustrated here), for example fixed body infrared detectors. These are typically detectors that measure the concentrations of $SO_2$ and $CO_2$.

The diffusor 32 can be formed as a disposable diffusor, which is disposed of after a combustion analysis carried out in the combustion furnace, but preferably consists at least substantially of silicon nitride, which is heat-resistant and easy to clean, and therefore the diffusor can advantageously be used a number of times. The diffusor 32 is fastened releasably to a diffusor carrier 36 and is illustrated in greater detail in FIG. 2.

Figure 2:
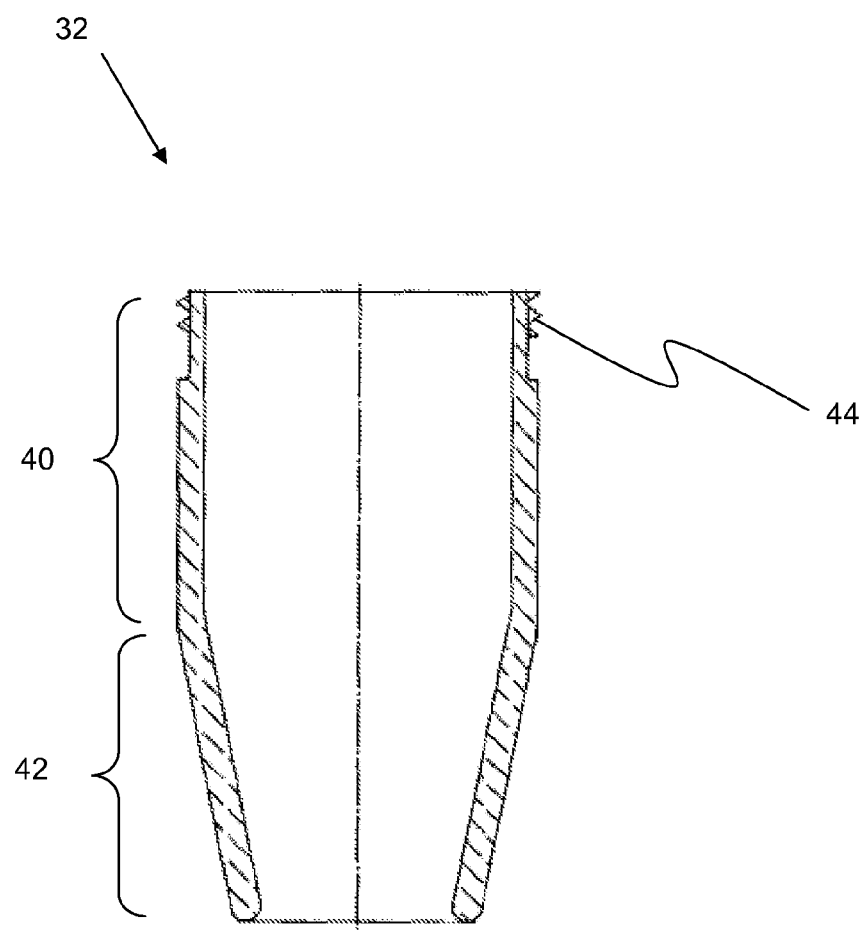
FIG. 2 shows a protective element formed in accordance with the invention in longitudinal section.

As can be seen clearly in FIG. 2, the diffusor 32 in this exemplary embodiment comprises a cylindrical portion 40 and a conical portion 42. Means 44 for releasable connection of the diffusor 32 to the diffusor carrier, more specifically in the form of an outer thread in the example illustrated in FIG. 2, are provided on the end portion facing towards the diffusor carrier in the normal operating state of the diffusor 32 in a furnace chamber, wherein the diffusor carrier is then provided with a corresponding inner thread. The diffusor 32 can also be fastened to a diffusor carrier in various other ways however.

As can be clearly seen in FIG. 1, the outer diameter of the free end of the conical portion of the diffusor 32 is dimensioned such that it is smaller than the inner diameter of a crucible 24 used during the combustion analysis, and therefore the diffusor in the normal operating state can protrude slightly into the crucible 24, but at the same time a gap remains between the outer edge of the diffusor and the inner edge of the opening of the crucible, it being possible for oxygen to reach the crucible via said gap during the combustion of a sample.

The sample carrier 22 and diffusor 32 are advantageously movable relative to one another, for example since the sample carrier is movable as indicated by the arrow 45. This makes it possible to adjust the spacing of the diffusor 32 from the sample carrier and to therefore adjust a sample or a crucible containing the sample arranged on the sample carrier, such that on the one hand material spatters produced during the combustion of the sample are collected as far as possible by the diffusor 32, but on the other hand it is ensured that sufficient oxygen reaches the sample. Here, the conical embodiment of the outer face of the portion of the diffusor 32 pointing towards the crucible 24 corrects relatively small positional errors of the crucible 24 on the sample carrier 22 when it is moved into the crucible after positioning of the crucible 24 on the sample carrier 22. After a measurement, the sample carrier can then be moved away again from the diffusor 32 for the purpose of easy removal of the crucible.

Since any spatters produced during the combustion of a sample, provided these do not remain in the crucible 24, are collected as far as possible by the diffusor 32, the cleaning of the furnace chamber is simplified considerably. If tungsten is used as a reaction accelerator, practically no health-damaging tungsten oxide is now found on the inner walls of the furnace chamber. Since spatters are no longer generally problematic however, pure iron can advantageously also be used as a reaction accelerator and is not only more cost effective compared to tungsten, but also forms iron oxide during the combustion process, which can be much more easily handled compared to tungsten oxide.

The combustion furnace 10 is designed such that combustion gases during operation of the combustion furnace 10 and also gases introduced into the furnace as described above can only escape via the gas outlet 33, as indicated by the arrow 47. Since the diffusor prevents material spatters produced during the combustion of a sample from clogging the gas inlets, these inlets can be arranged closer to the sample and the volume of the furnace chamber 11 can be reduced. A smaller volume however also means that less gas has to be used to flush the furnace between two measurements and that the downtime between two successive measurements can be reduced.

Figure 3:
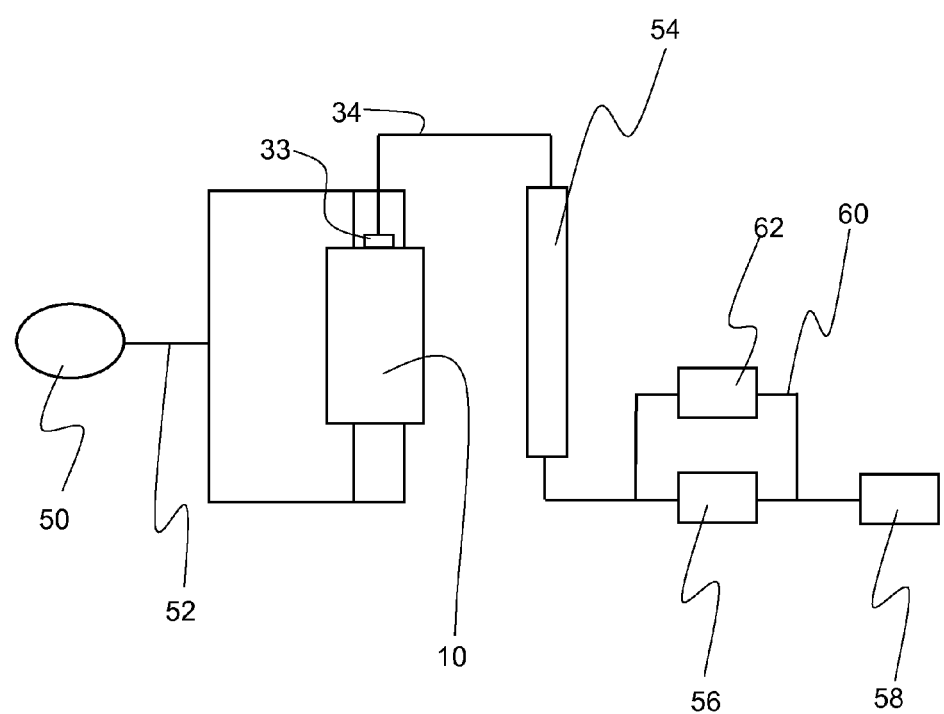
FIG. 3 shows a highly schematic view of the basic arrangement of the typical components of a device according to the invention for combustion analysis.

The basic arrangement of the typical components of a device according to the invention for combustion analysis is shown in FIG. 3 in a highly schematic manner. A carrier gas source 50, generally in the form of an oxygen cylinder, is connected via a corresponding line 52 to the gas inlets of the induction furnace 10. Here, the ratio of the gases to be introduced into the induction furnace from above to those to be introduced from below can be adjustable.

A sample line 34, in which the particle filter 54 is incorporated, is connected to the gas outlet 33 of the induction furnace 10. Downstream of the filter 54 is arranged a pressure controller 56, by means of which the flow rate of the gases in the sample line during a measurement can be adjusted such that detectors 58, of which only one is shown here by way of example, arranged downstream of the pressure controller 56 can be operated in an optimal manner.

In the exemplary embodiment illustrated, when the arrangement is flushed, the pressure controller 56 may advantageously be bypassed via a bypass line 62, which can be opened and closed by means of a bypass valve 64. This allows the arrangement to be flushed with a high flow rate between two measurements, without having to change the calibrated setting of the pressure controller 56 for this purpose. Typical flow rates during measurements lie for example, depending on the detector, in the range from approximately 3 to 4 liters per minute, whereas, during flushing, flow rates between approximately 8 and 10 liters per minute can be set by opening the bypass valve 64, which reduces the flushing time and therefore the downtime between two successive measurements.

With a device according to the invention, the previously conventional continuous flow of carrier gas through the device in what is known as standby mode can be omitted. The device is only flushed with carrier gas shortly before a measurement. Since, in addition, the entire volume through which gas flows can be considerably reduced in the device according to the invention compared to known devices, considerable savings in the gas consumption have been demonstrated in initial tests with devices according to the invention.

Figure 4:
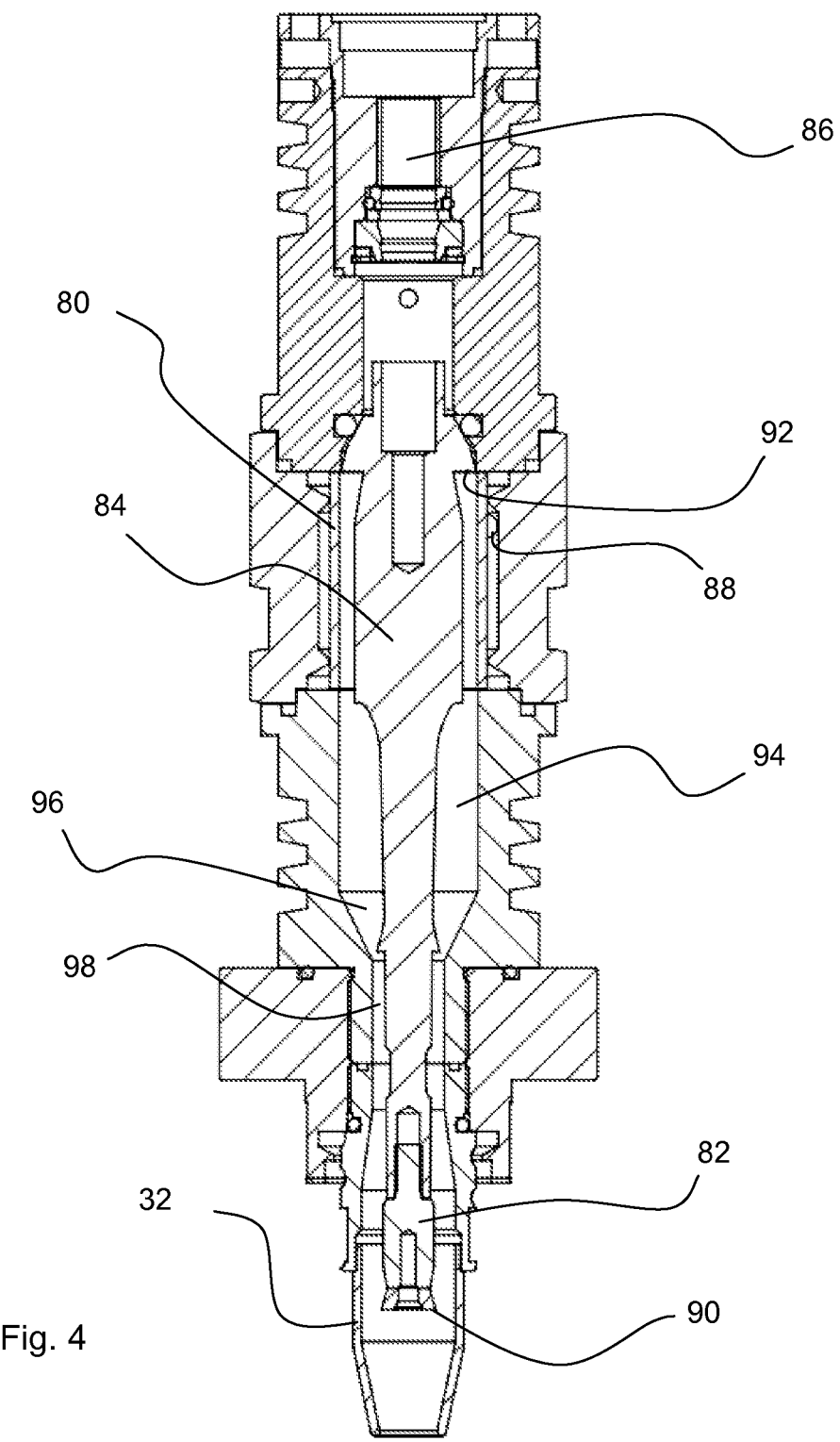
FIG. 4 shows a longitudinal section through some key parts of a device formed in accordance with the invention in a second embodiment, in which a cleaning device for automatic cleaning is provided, which is located in a first position.
Figure 5:
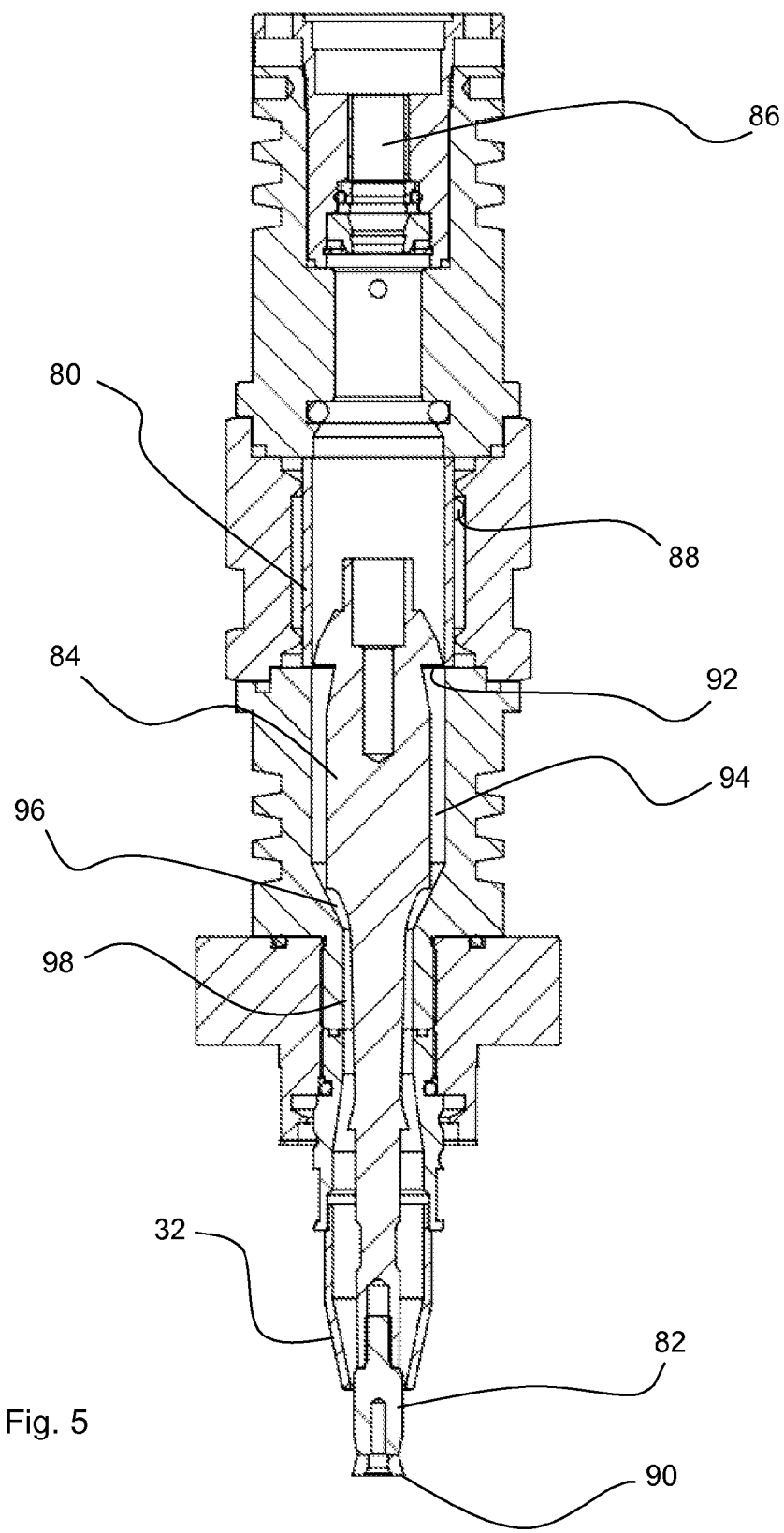
FIG. 5 shows a longitudinal section through the device according to FIG. 4, in which the cleaning device is moved into a second position however.

Details of a second embodiment of a device according to the invention are shown in FIGS. 4 and 5, wherein, for reasons of clarity, the parts already described in conjunction with FIGS. 1 to 3, in particular parts of the furnace chamber and of the sample container, are not illustrated. A diffusor 32 according to the invention, a particle filter 80 and means for automatic cleaning of the diffusor 32 and of the filter 80 are shown, wherein these means, in the exemplary embodiment, comprise a ram 82 for cleaning the diffusor, a ram 84 for cleaning the filter, and means for moving the rams, for example here in the form of a hydraulic or pneumatic unit 86.

In FIG. 4, the rams are shown in a first position, or what is known as the rest position, in which they release the path of the combustion gases to a gas outlet 88, such that gases produced during the combustion of a sample in the furnace pipe (not shown here) can reach the gas outlet 88 via the diffusor 32 through the particle filter 80, which is cylindrical in this case. The filter 80 is preferably a sintered metal filter, which filters out any solid particles in the combustion gas.

In FIG. 5, the rams are shown in a second position, in which they are moved at the end of a cleaning process through the diffusor 32 (ram 82) or through the filter 80 (ram 84).

The ram 82 is connected releasably to the ram 84 in this exemplary embodiment, such that the ram 82 can be easily exchanged as required. Each ram 82 and 84 has a peripheral protrusion 90 and 92 respectively, which is matched to the respective parts to be cleaned and is used to scrape any contaminations on the inner face of the mouth of the diffusor 32 facing towards the sample carrier and on the inner face of the particle filter 80 respectively.

An expansion chamber 94 is provided between the filter 80 and diffusor 32 and opens out via a conical portion 96 into a connecting chamber 98 between the expansion chamber and diffusor 32. Due to this embodiment with a conical portion 96, it is advantageously ensured when the cleaning process is carried out that, as the filter 80 is scraped, particles falling off fall into the diffusor 32 and via the diffusor 32, acting then as a funnel, into the crucible (not illustrated here), in which the sample has been burned, provided the crucible is still fitted in position. Since the crucibles are generally disposable crucibles, they can advantageously be disposed of easily after the combustion and cleaning processes.

Numerous modifications and developments, which for example concern advantageous additional modules for the user, are possible within the scope of the inventive concept. Means for measuring the flow rate of a gas conveyed from the combustion furnace via the gas outlet, which are arranged for example in the sample line and generate an alarm signal if the gas flow rate falls below a predefinable minimum valve, which indicates a blockage in the line, can thus be provided.

A control and evaluation unit can advantageously also be provided, which is coupled to means for measuring the pressure of the carrier gas introduced into the induction furnace and is designed, when a predefined maximum pressure is exceeded, to generate an alarm signal in order to prevent the furnace chamber from becoming untight during a measurement process and to prevent gases from leaving the chamber in an uncontrolled manner. Here, the alarm signal can also be used to automatically interrupt the carrier gas supply.

Furthermore, the differential pressure of the gases fed to the induction furnace and the gases derived from the furnace can be measured, for example by means of a differential pressure sensor. The differential pressure can then be compared with a predefined limit value in order to conclude that there is a disturbance, in particular a contamination/blockage, in the event that the limit value is exceeded and to generate a corresponding alarm signal.

The protective element according to the invention can also be retrofitted in existing induction furnaces for combustion analysis that are suitable for refitting, wherein the protective element then replaces the lance normally provided above the point of combustion in such furnaces for feeding oxygen and is connected to the gas inlet previously coupled to the lance. This prior gas inlet is connected to the sample line and to the gas outlet. The prior gas outlet can be closed or converted to form an additional gas inlet. With an induction furnace retrofitted in such a way, not only is the volume of the furnace chamber then reduced, but the cleaning process is also considerably simplified and the use of iron as a reaction accelerator is possible.

The invention claimed is:

1. A device for combustion analysis, comprising:
a movable sample carrier;
an induction furnace with a furnace chamber, in which carrier gas can flow during operation via at least one gas inlet to a gas outlet, and in which a sample to be analyzed can be arranged and burned in a sample container; and
a hollow protective element which in normal operation of the device, is arranged in the furnace chamber directly above the sample such that an end of the protective element facing towards the sample, together with the sample container, forms a constriction for the carrier gas flow, said constriction directing said carrier gas flow towards said sample, wherein the protective element conveys gases produced during the combustion of the sample through the protective element and to the gas outlet; and
wherein a spacing between the sample container and the hollow protective element is selectively adjustable by an up-and-down movement of the sample carrier,
wherein the hollow protective element is formed as a diffusor comprising a cylindrical portion and a conical portion, a smallest outer diameter of the conical portion being smaller than an inner diameter of an opening of the sample container, and an upward movement of the sample carrier positions the conical portion of the diffusor at the opening of the sample container.

2. The device according to claim 1 wherein the hollow protective element consists at least substantially of silicon nitride.

3. The device according to claim 1, further comprising:
a pressure controller, wherein the pressure controller comprises a flow rate measuring device that measures a flow rate of a gas conveyed via the gas outlet, and
a pressure measuring device that measures a pressure of the carrier gas introduced into the furnace chamber; and
a control and evaluation unit coupled to the pressure controller, wherein the control and evaluation unit generates an alarm signal when the carrier gas introduced into the furnace chamber exceeds a defined maximum pressure.

4. The device according to claim 3, further comprising:
a bypass line that bypasses the pressure controller; and
a bypass valve, wherein the pressure controller, the bypass line and the bypass valve are arranged in a line downstream of the gas outlet.

5. The device according to claim 1, further comprising:
a ram with a scraping protrusion that is operable to automatically clean at least the hollow protective element.

6. The device according to claim 1 wherein the hollow protective element consists at least substantially of silicon nitride.

7. A device for combustion analysis, comprising:
a sample container to hold a sample to be analyzed;
an induction furnace including a furnace chamber, a sample carrier, at least one gas inlet and a gas outlet, the sample carrier having a surface to hold the sample container and moveably mounted in the furnace chamber; and
a hollow protective element which is arranged in the furnace chamber directly above the sample container such that an end of the protective element that faces the sample container, together with the sample container, forms a constriction for a carrier gas flow, the constriction which directs the carrier gas flow towards the sample in the sample container, wherein the protective element conveys gases produced during the combustion of the sample through the protective element and to the gas outlet and wherein a spacing between the sample container and the hollow protective element is selectively adjustable by movement of the sample carrier, and an upward movement of the sample carrier positions the conical portion of the diffusor at the opening of the sample container.

* * * * *